US006218581B1

(12) United States Patent
Nagaoka

(10) Patent No.: US 6,218,581 B1
(45) Date of Patent: Apr. 17, 2001

(54) PROCESS OF PRODUCING OPTICALLY ACTIVE ALCOHOL

(75) Inventor: Hiroyuki Nagaoka, Maebashi (JP)

(73) Assignee: Sanyo Shokuhin Co., Ltd., Tokyo (JP)

( * ) Notice: Subject to any disclaimer, the term of this patent is extended or adjusted under 35 U.S.C. 154(b) by 0 days.

(21) Appl. No.: 09/367,137

(22) PCT Filed: Dec. 28, 1998

(86) PCT No.: PCT/JP98/06005

§ 371 Date: Aug. 6, 1999

§ 102(e) Date: Aug. 6, 1999

(87) PCT Pub. No.: WO99/34010

PCT Pub. Date: Jul. 8, 1999

(30) Foreign Application Priority Data

Dec. 29, 1997 (JP) .................................................. 9-369499

(51) Int. Cl.[7] .......................... C07C 29/09; C07C 29/136; C07C 29/143; C07C 29/147; C07C 29/48
(52) U.S. Cl. .......................... 568/648; 568/715; 568/810; 568/812; 568/814; 568/815
(58) Field of Search .................................... 568/648, 715, 568/810, 812, 814, 815

(56) References Cited

FOREIGN PATENT DOCUMENTS

| | | |
|---|---|---|
| 4-222592 | 8/1992 | (JP) . |
| 8-103289 | 4/1996 | (JP) . |
| 2756790 | 3/1998 | (JP) . |
| 2774341 | 4/1998 | (JP) . |
| 2784578 | 5/1998 | (JP) . |
| 2804247 | 7/1998 | (JP) . |
| 10-210981 | 8/1998 | (JP) . |

OTHER PUBLICATIONS

Chem. Pharm. Bull. 43 (9) 1458–1461 (1995).
J. Chem. Soc. Perkin Trans. –1, 1995, pp. 1295–1298.
"Organic Chemistry for Biology 3–Proteins" ed. Kazuo Satake, pp. 114–172 (1965).
Phytochemistry, vol. 30, No. 11, pp. 35–3497, (1991).

*Primary Examiner*—Peter O'Sullivan
(74) *Attorney, Agent, or Firm*—Merchant & Gould P.C.

(57) ABSTRACT

The present invention relates to a process of producing optically active alcohol having high optical purity by performing an enzyme conversion reaction on a raw material serving as the substrate, examples of which include racemic alcohol, ketone and the acylated form of a racemic alcohol, followed by hydrolysis as necessary, using as an optical separation catalyst a immobilized water-soluble protein extracted from inexpensive and safe grains or beans in order to solve the problems of the reaction process consisting of low yield due to the occurrence of side reactions, detrimental effects on the ecosystem and their accompanying cost burden, the need for aseptic procedures and the extended amount of time of subculturing, all of which are problems associated with production processes of optically active alcohols of the prior art that use microorganisms, microorganism enzymes, animal tissue enzymes and cultured plant cells.

6 Claims, 1 Drawing Sheet

PROCESS OF PRODUCING OPTICALLY ACTIVE ALCOHOL

This application is a 371 of PCT/JP98/06005 filed Dec. 28, 1998.

TECHNICAL FIELD

The present invention relates to a process of producing optically active alcohol from a substrate using an immobilized water-soluble protein component, extracted from grains, beans and other plant resources, as a catalyst.

BACKGROUND ART

Optically active alcohols are extremely important substances as raw materials or intermediate raw materials for pharmaceuticals and agricultural chemicals as well as intermediates, in the field of fine chemicals, for products such as ferroelectric liquid crystals.

Known processes for producing optically active alcohols of the prior art are reacting a substrate with 1) microorganisms, 2) enzymes derived from microorganisms, 3) enzymes derived from animal tissue, and 4) cultured plant cells for biosynthesis of an optically active substance such as optically active alcohol.

The process using microorganisms of 1) above is a technique for obtaining optically active alcohol by reacting a substrate with cultured microorganisms, a known example of which is disclosed in Japanese Patent No. 2784578 (a process of producing optically active 1,2-diols).

In addition, the process using an enzyme derived from microorganisms of 2) above is a technique for obtaining optically active alcohol by reacting a substrate with a homogenized liquid of microorganisms cultured by introducing a gene, a known example of which is disclosed in Japanese Unexamined Patent Publication No. 10-210981 (novel protein that catalyzes conversion from halohydrin to optically active diol).

In addition, the process using an enzyme derived from animal tissue of 3) above is a technique for obtaining optically active alcohol by reacting a substrate with a protein isolated from animal tissue, a known example of which is disclosed in Japanese Patent No. 2756790.

In addition, the reaction using cultured plant cells of 4) above is a technique for obtaining optically active alcohol by reacting a substrate with plant cells, an example of which is reported in the literature (Chem. Pharm. Bull., 43, pp. 1458–1461).

As is known in Japanese Patent No. 2784578 (a process of producing optically active 1,2-diols) and Japanese Patent No. 2774341 (a process of producing an optically active 2-hydroxy acid derivative), processes using the "microorganisms" of 1) above synthesize optically active alcohol by growing microorganisms in a culture solution by appropriately setting culture conditions, treating this culture liquid by centrifugal separation or filtration to collect the microorganisms, and asymmetrically reducing a ketone body, which is used as a substrate, in a liquid in which the microorganisms have been suspended in 0.1 M phosphate buffer (pH 6.5) or distilled water and so forth. Since side reactions other than the substrate conversion reaction occur simultaneously caused by the diverse types of enzymes contained in the microorganisms, the yield of the target optically active alcohol is low. In addition, even if isolation and purification work to remove the target optically active alcohol from a solution containing the reaction product, due to the low purity of the resulting optically active alcohol, it is difficult to use as a synthesis intermediate in the field of fine chemicals. As disclosed in Japanese Unexamined Patent Publication No. 10-210981 (novel protein for catalyzing conversion from halohydrin to optically active diol), processes using "enzymes derived from microorganisms" of 2) above are processes for producing optically active epihalohydrins and optically active diols by using a transformed microorganism in which genes cloned by gene recombination techniques are present in large numbers in the microorganisms. Since there are no large differences in the reaction process itself from processes using microorganisms, side reactions that take place during substrate reaction cannot be controlled, thereby causing this process to have the same problems as processes using "microorganisms". Moreover, since gene-introduced microbial strains are heterogenous varieties in the natural world, there is the risk of having detrimental effects on humans and other members of the ecosystem. Consequently, a cost burden is required for equipment for isolating from the external environment as well as incineration treatment of reaction residue and so forth. In addition, as is known in Japanese Patent No. 2756790 (a process of producing optically active cyclopentenol derivative), processes using "enzymes derived from animal tissue" of 3) above are processes for producing optically active cyclopentenol derivative using an asymmetrical hydrolysis reaction of porcine pancreatic lipase. As is described in "Organic Chemistry for Biology 3—Proteins" edited by Kazuo Satake, pages 114–172 (Asakura Shoten Publishing), since enzymes derived from animal tissue are crude enzymes, side reactions occur in the same manner as 1) and 2) above, resulting in an unavoidable decrease in yield. In addition, processes using "cultured plant cells" of 4) above have the problem of low yield of optically active alcohol due to side reactions other than the substrate conversion reaction that occur caused by the diverse types of enzymes contained in plants. In addition, raising of cultured plant cells is difficult as is indicated by the need for sterile procedures throughout the entire process. Moreover, an amount of time for repeating subculturing of 1 to 2 years along with preparation of reaction nutrient culture liquid (such as MS medium) for reacting with substrate are required, thereby creating the shortcoming of a complex reaction procedure.

DISCLOSURE OF THE INVENTION

In order to solve the above-mentioned problems, the object of the present invention is to provide a production process for obtaining optically active alcohol of high optical purity that is applied to organic synthesis chemistry by using, as an optical separation catalyst, a water-soluble protein extracted from inexpensive grains and beans that are produced worldwide, is friendly to the ecosystem, and allows a considerable reduction in reaction costs.

The production process for obtaining optically active alcohol of high optical purity by using the above-mentioned optical separation catalyst in the present invention generally includes the processes indicated below.

(1) A process for producing optically active alcohol comprising selectively oxidizing a substrate in the form of one enantiomer of a racemic alcohol to obtain ketone, allowing the other enantiomer to remain unreacted, and separating the optically active alcohol.

(2) A process for producing optically active alcohol comprising asymmetric reduction of a substrate in the form of a ketone molecule.

(3) A process for producing optically active alcohol comprising asymmetric hydrolysis of a substrate in the acylated form of a racemic alcohol.

(4) A process for producing optically active alcohol comprising selectively acylating one enantiomer of a racemic alcohol in an organic solvent, hydrolyzing the resulting acylated enantiomer, and separating the optically active alcohol.

As a result of conducting earnest research on a process for obtaining optically active alcohol of high optical purity that solves the above-mentioned problems and is safe and is easy, the inventors of the present invention found that the R or S form of optically active alcohol of high purity that can be sufficiently used as a raw material for the synthesis of synthesis intermediates in the field of fine chemicals can be obtained both safely and easily by combining a first step comprising extracting water-soluble protein from grains or beans, a second step comprising immobilization of the above-mentioned protein, a third step comprising performing an enzyme conversion reaction on a substrate using the above-mentioned immobilized protein as catalyst, a fourth step comprising extracting a mixture of the above-mentioned reaction substrate converted by said third step and the reaction product with organic solvent, and a fifth step comprising isolating and purifying optically active alcohol or the acylated form of optically active alcohol from the extract of said fourth step, followed additionally by hydrolysis as necessary, thereby leading to completion of the present invention.

Although examples of grains or beans that can be used in the present invention include grains such as buckwheat, amaranth, rice, wheat, barley, corn, oats, rye, foxtail millet, barnyard millet, millet, adlay and sorghum, or beans such as adsuki beans, kidney beans, green peas, green beans and soy beans, they are not limited to these.

In the extraction of water-soluble protein in the first step of the present invention, grains or beans are crushed, large pieces and husks are removed and the finely crushed grains or beans obtained in this manner are extracted for 30 minutes or more in water equal to 7–15 times the weight of the crushed flour of grains or beans at about 20–60° C., and preferably about 40° C. and a pH of about 6–8, and preferably pH 7.0. It is most effective to extract for about 45 minutes, and even if extracted for longer than this, the amount of extract does not change. When it is necessary to adjust pH, pH may be adjusted to the above-mentioned optimum range using a food-grade acid such as $H_2SO_4$, HCl or $H_3PO_4$ or a food-grade base such as NaOH. The above-mentioned water-soluble protein extract or protein curd obtained by separating food fiber components from this extract by decanting or centrifugal separation, is either transferred directly to the second step, or transferred to the second step after being formed into a powder by spray drying, freeze-drying or vacuum-drying and so forth and then redissolving as necessary.

However, when it is necessary to treat a large amount of protein, the above-mentioned protein curd is subjected to isoelectric point treatment using a food-grade acid such as $H_2SO_4$, HCl or $H_3PO_4$ or a food-grade base such as NaOH followed by separation of the whey by decanting or centrifugal separation to obtain protein curd. This isoelectric precipitation is performed for the purpose of concentrating water-soluble protein, and effects, after the treatment, are demonstrated that are similar to the case of forming into a powder by direct spray-drying and so forth of water-soluble protein extract. The object of selecting the pH of isoelectric point precipitation is to select the fraction having the largest precipitated amount, and is in the vicinity of pH 4.5 in the case of soy bean and green pea protein and pH 9.5 in the case of buckwheat. 5–10 times by weight of water are added to this curd followed by crushing, using a mixer or stirrer to prepare a protein slurry, and neutralization (pH 6–8) to obtain a neutral slurry. After converting this slurry into a powder by spray-drying, freeze-drying or vacuum-drying and so forth in the same manner as previously described, the powder is redissolved and transferred to the second step.

However, in order to prevent deactivation by thermal denaturation of a protein, namely the enzyme involved in the conversion reaction, with respect to the heating conditions when performing spray-drying, the temperature must be set to a temperature that prevents the temperature of said protein extract itself from exceeding 80° C.

In the second step, examples of processes for immobilizing said extracted protein include: 1) a carrier coupling process in which said extracted protein is coupled to a water-insoluble carrier, e.g. derivative of a polysaccharide, such as cellulose, dextran or agarose, and polyacrylamide gel; 2) a crosslinking process in which said extracted protein is immobilized by forming crosslinking bonds between said extracted proteins using a reagent having at least two functional groups; 3) and an encapsulating process in which said extracted protein is either incorporated in the fine matrix of a gel such as arginate, starch, konjak (devil's tongue jelly), polyacrylamide gel or a gel of polyvinyl alcohol and so forth (matrix type) or coating with a semi-permeable coating (microcapsule type). Any of these immobilization processes can be used in the present invention. However, an encapsulating immobilization process using the salt of alginic acid extracted from kelp is friendly to the environment and has the easiest immobilization procedure, thereby making it the most preferred process.

In the third step, examples of enzyme conversion processes for obtaining optically active alcohol or the acylated form of optically active alcohol from a substrate serving as the raw material are described below.

(1) A process for obtaining optically active alcohol comprising selectively oxidizing a substrate in the form of one enantiomer of a racemic alcohol to obtain ketone, and allowing the other enantiomer to remain unreacted as optically active alcohol.

(2) A process for producing optically active alcohol comprising asymmetric reduction of a substrate in the form of a ketone molecule.

(3) A process for producing optically active alcohol comprising asymmetric hydrolysis of a substrate in the acylated form of a racemic alcohol.

(4) A process for obtaining optically active alcohol comprising three-dimensional acylation by acyl halide or vinyl acetate of one enantiomer of a substrate in the form of a racemic alcohol in an organic solvent.

In these reactions:
  in the asymmetric reduction reaction using the ketone molecule of (2) as substrate, since the asymmetric reduction reaction of enzyme conversion stops without reaching 100%, if an extraction treatment is not performed on the reaction solution when the reaction has stopped or before it stops, optical purity decreases with time. Although it is therefore necessary to determine the reaction stopping time according to the type of grain or bean and, if the reaction is terminated at a conversion rate of about 20%, the steric configuration and optical purity of the resulting optically active alcohol are similar to the case of (1) using racemic alcohol for the substrate. In the reaction of (3) using an acylated form of a racemic alcohol for the substrate, since optical purity decreases if the conversion efficiency of the asymmetric hydrolysis reaction exceeds about 20%, it is necessary to determine the reaction stopping time according to the type of grain or bean. Although the yield is low, in the case of terminating the reaction at a conversion rate of about 20%, the steric configuration and optical purity of the resulting optically active alcohol is similar to the case of (1) using a racemic alcohol for the substrate. In addition, the reaction of (4) using asymmetric acylation by an asymmetric acylation reaction allows obtaining of optically active alcohol by further hydrolyzing the acylated form obtained from the asymmetric acylation reaction. However, since optical purity decreases if the conversion rate of the asymmetric acylation reaction exceeds about 20%, it is necessary to determine reaction stopping time according to the type of grain or bean. When the acylation reaction is terminated at a conversion rate of about 20%, the steric configuration and optical purity of the resulting optically active alcohol obtained by the following hydrolysis is similar to the case of (1) using racemic alcohol for the substrate. In the present invention, the process of (1) for obtaining optically active alcohol by selectively oxidizing one enantiomer using a racemic alcohol for the substrate is the most preferable in terms of yield and so forth. The suitable reaction temperature of (1) through (4) above is about 25–45° C., and preferably 30–40° C., and these reactions are most preferably carried out at about 35° C. In addition, in the reactions of (1) through (3) above, although water can be used as a polar solvent or acetone, methanol or ethanol can be used as a nonpolar solvent, the polar solvent water is most preferable. Although organic solvents such as benzene, toluene, heptane, isopropyl alcohol (dry) and so forth can be used in the reaction of (4), it is preferable to use benzene. Although reaction time differs according to the substrate, the origin of the water-soluble protein and the type of reaction, it is about 2–15 days, and as previously described, the reactions of (2) through (4) are terminated at the point the conversion rate has reached about 20%.

In addition, optically active alcohols obtained by these reactions consist of the S form or R form depending on the effects of the substituent groups of the substrate.

Non-reactive solvents such as ethyl acetate, diethyl ether and dichloromethane can be used for the extraction organic solvent in the fourth step.

Although it is most preferable to use silica gel chromatography or silica gel thin layer chromatography for the isolation and purification procedure in the fifth step, as is described in Japanese Patent No. 2804247 (reaction using an immobilized biocatalyst), an isolation and purification process known prior to filing of the present application can be used, such as an isolation and purification process in which a portion of the product-rich reaction solution is removed from the reaction tank, the reaction solution is transferred to a crystallization tank set to the precipitation temperature of the product to precipitate the product, substrate is added to the mother liquor after separation by filtration, the solution is returned to the reaction tank and a series of reaction procedures are repeated to accumulate the product in the crystallization tank in the form of a suspension.

BEST MODE FOR CARRYING OUT THE INVENTION

Figure 1:
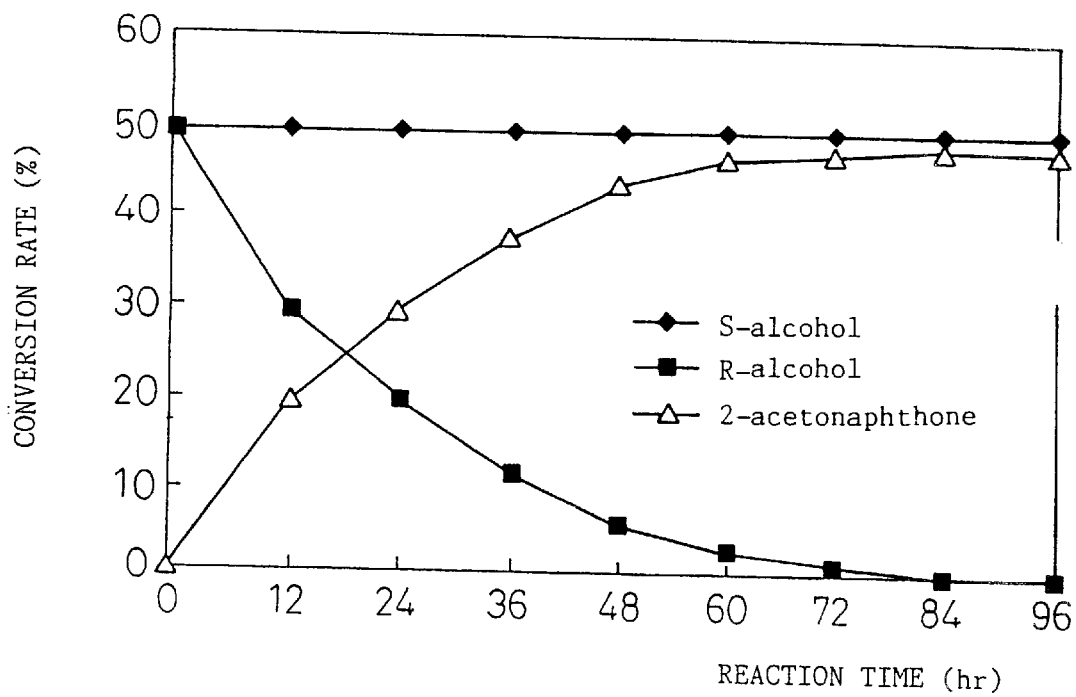
FIG. 1 is a graph indicating the relationship between reaction time and formation conversion rate of (S)-1-(2-naphthyl)ethanol by way of bioconversion to 2-acetonaphthone accompanying sterically selective oxidation of (R)-1-(2-naphthyl)ethanol of the substrate racemer in the form of 1-(2-naphthyl)ethanol.

Although the following provides a detailed explanation of the present invention based on its examples, this is provided only for the sake of explanation, and should not be understood to limit the present invention in any way.

Process of Producing Optically Active Alcohol by Selectively Oxidizing One Enantiomer of a Racemic Alcohol as Substrate of (1)

EXAMPLE 1 (GREEN PEA WATER-SOLUBLE PROTEIN)

As the first step, green peas are crushed, the husks are removed and a green pea water-soluble protein component dissolved for about 45 minutes in 9 times by weight of distilled water (about 40° C.) at a pH of about 7.0 is adjusted to pH 7.0 using aqueous NaOH. The food fiber, the precipitated component, is removed and the protein is subjected to isoelectric point precipitation by bringing the water-soluble protein portion to acidic conditions (about pH 4.5). After redissolving the protein precipitate with distilled water at pH 7.0, spray-drying treatment is performed on the resulting green pea water-soluble protein solution (sample concentration: 5.0%) to prepare powdered green pea protein. In addition, an aqueous sodium arginate solution is prepared by dissolving sodium arginate in aqueous solution under autoclave conditions and temperature of 121° C. for 20 minutes.

Next, in the second step, 200 ml of distilled water corresponding to ten times the equivalent weight are added to 20 g of green pea protein powder followed by the addition of 250 ml of 5% aqueous sodium arginate solution corresponding to 1.5 times the equivalent weight and stirring to uniformity. The resulting green pea-sodium arginate mixed solution is dropped into 0.6% aqueous calcium chloride solution using a syringe and so forth to prepare calcium arginate gel beads containing green pea protein in the immobilized state. Moreover, the bead film is strengthened by allowing it to stand for at least 5 hours in 0.6% aqueous calcium chloride solution.

Continuing, in the third step, the green pea-calcium arginate gel beads are sufficiently washed with distilled water to remove aqueous calcium chloride solution, followed by the addition of reaction solution in the form of distilled water corresponding to 20 times the equivalent weight of green pea protein powder (400 ml) used. After making the temperature of the distilled water 35° C. using a constant-temperature shaking incubator, substrate racemic alcohols in the form of 1-(4-bromophenyl)ethanol, 1-(4-chloropheny)ethanol, 1-(4-methyphenyl)ethanol, 1-(4-methoxyhenyl)ethonaol, 1-(4-nitrophenyl)ethanol 1-phenylethanol and 1-(2-naphthyl)ethanol were added followed by substrate conversion by respectively setting the conditions of the shake incubator to 55 rpm.

In the fourth step following completion of the reaction, after roughly separating the beads and reaction solvent portion and sufficiently washing the beads with a solvent such as distilled water, the reaction solvent portion containing the washing solvent liquid, reaction substrate and reaction product was extracted with diethyl ether. Moreover, after washing the ether layer with saturated brine, the ether layer was dehydrated and dried with sodium sulfate and allowed to stand.

Finally, in the fifth step, the diethyl ether layer was removed using an evaporator, and the target optically active alcohol was isolated and purified from the reaction substrate and reaction product with a developing solvent containing hexane and ethyl acetate in a ratio of 9:1 using a silica gel chromatograph of 70–230 mesh.

The steric configuration of the isolated optically active alcohol was determined from a comparison between the value (+ or −) obtained by referring to the literature (J. Chem. Soc. Perkin Trans. 1, 1995, pp. 1295–1298 and Photochemistry, Vol. 30, No. 11, pp. 3595–3597) and the angle of rotation of the resulting optically active alcohol. The retention times of the S form and R form steric configurations of substrates consisting of (±)-1-(4-bromophenyl)ethanol and (±)-1-(4-chlorophenyl)ethanol were confirmed by high-performance liquid chromatography (HPLC) analysis conditions of a chiral cell OB of 0.46 cm in diameter×25 cm (Daicel Chemical Industries): 30°, UV 254 nm, eluate: hexane:2-propanol=9:1 and flow rate of 0.5 ml/min, and substrates consisting of (±)-1-(4-methoxyphenyl)ethanol and (±)-1-(4-nitrophenyl)ethanol were able to be confirmed by high-performance liquid chromatography (HPLC) analysis conditions of chiral cell OB of 0.46 cm in diameter×25 cm (Daicel Chemical Industries), 30°, UV 254 nm, eluate: hexane:2-propanol=9:1 and flow rate of 1.0 ml/min. The difference between the integral ratios of both mirror images of the S form and R form steric configurations that appear in HPLC was determined as the optical purity (e.e.=enantiomer excess).

By using the equipment analysis described above, the retention times of (±)-1-(4-bromophenyl)ethanol were confirmed to be 10.447 for the S form and 11.031 for the R form, those of (±)-1-(4-chlorophenyl)ethanol 9.936 for the S form and 10.355 for the R form, those of (±)-1-phenylethanol 11.958 for the S form and 13.133 for the R form, those of (±)-1-(2-naphthyl)ethanol 15.693 for the S form and 17.049 for the R form, those of (±)-1-(4-methoxyphenyl)ethanol 9.165 for the S form and 10.781 for the R form, and those of (±)-1-(4-nitrophenyl)ethanol 18.923 for the R form and 19.562 for the S form. In addition, the retention times of 4-bromoacetophenone, 4-chloroacetophenone, 4-methoxyacetophenone and 4-nitroacetophenone that are formed by oxidation of each substrate were similarly confirmed to be 13.122, 10.304, 17.169 and 37.208, respectively.

Synthesis of (S)-1-(4-bromophenyl)ethanol

As shown here, the biochemical conversion reaction of immobilized green pea protein for the substrate (±)-1-(4-bromophenyl)ethanol (200 mg) requires 8 days by going through bioconversion to 4-bromoacetophenone accompanying sterically selective oxidation of (R)-1-(4-bromophenyl)ethanol to obtain 114 mg of (S)-1-(4-bromophenyl)ethanol at a yield of 57%. Optical purity was obtained at 88% e.e. The reaction course and time at completion of reaction were determined by GC using the Hitachi Model G-3500 gas chromatograph under conditions consisting of carrier gas: He at 0.48 ml/min, split ratio: 1/55, oven temperature: 150° C., inlet temperature: 250° C., outlet temperature: 250° C., pressure: 136, flow rate value: 42, analytical column: TC-5HT 0.25 mm I.D.×30M df (GL Science).

Synthesis of (S)-1-(4-chlorophenyl)ethanol

As shown here, the biochemical conversion reaction of immobilized green pea protein for the substrate (±)-1-(4-chlorophenyl)ethanol (200 mg) requires 8 days by going through bioconversion to 4-chloroacetophenone accompanying sterically selective oxidation of (R)-1-(4-chlorophenyl)ethanol to obtain 84 mg of (S)-1-(4-chlorophenyl)ethanol at a yield of 42%. Optical purity was obtained at 87% e.e.

Synthesis of (S)-1-(4-methoxyphenyl)ethanol

As shown here, the biochemical conversion reaction of immobilized green pea protein for the substrate (±)-1-(4-methoxyphenyl)ethanol (200 mg) requires 7 days by going through bioconversion to 4-methoxyacetophenone accompanying sterically selective oxidation of (R)-1-(4-methoxyphenyl)ethanol to obtain 96 mg of (S)-1-(4-methoxyphenyl)ethanol at a yield of 48%. Optical purity was obtained at 95% e.e. Furthermore, HPLC conditions were set at a flow rate of 1.0 ml/min, while GC conditions were set to an oven temperature of 190° C.

Synthesis of (R)-1-(4-nitrophenyl)ethanol

As shown here, the biochemical conversion reaction of immobilized green pea protein for the substrate (±)-1-(4-nitrophenyl)ethanol (200 mg) requires 4 days by going through bioconversion to 4-nitroacetophenone accompanying sterically selective oxidation of (S)-1-(4-nitrophenyl)ethanol to obtain 76 mg of (R)-1-(4-nitrophenyl)ethanol at a yield of 38%. Optical purity was obtained at 54% e.e. HPLC conditions were set at a flow rate of 0.5 ml/min, while GC conditions were set to an oven temperature of 190° C.

Synthesis of (S)-1-phenylethanol

As shown here, the biochemical conversion reaction of immobilized green pea protein for the substrate (±)-1-phenylethanol (201 mg) requires 6 days by going through bioconversion to acetophenone accompanying sterically selective oxidation of (R)-1-phenylethanol to obtain 122 mg of (S)-1-phenylethanol at a yield of 61%. Optical purity was obtained at 98% e.e.

Synthesis of (S)-1-(2-naphthyl)ethanol

As shown here, the biochemical conversion reaction of immobilized green pea protein for the substrate 1-(2-naphthyl)ethanol (201 mg) requires 4 days by going through bioconversion to 2-acetonaphthone accompanying sterically selective oxidation of (R)-1-(2-naphthyl)ethanol to obtain 100 mg of (S)-1-(2-naphthyl)ethanol at a yield of 50% at an optical purity of 99% e.e. or higher (see FIG. 1).

Next, the results of synthesizing the above-mentioned optically active alcohols using immobilized green pea protein as optical separation catalyst are shown in the following table.

| | Grain and Bean Protein Green Peas | Optically Active Alcohol (Chiral Product) | Yield (%) | Optical Purity (% e.e.) |
|---|---|---|---|---|
| 1 | Pisum sativum L. | (S)-1-(4-bromophenyl)ethanol | 57 | 88 |
| 2 | Pisum sativum L. | (S)-1-(4-chlorophenyl)ethanol | 42 | 87 |
| 3 | Pisum sativum L. | (S)-1-(4-methoxyphenyl)ethanol | 48 | 95 |
| 4 | Pisum sativum L. | (R)-1-(4-nitrophenyl)ethanol | 38 | 54 |
| 5 | Pisum sativum L. | (S)-1-phenylethanol | 61 | 98 |
| 6 | Pisum sativum L. | (S)-1-(2-naphthyl)ethanol | 51 | 99 |

On the basis of the above, green pea water-soluble protein was found to be effective as an optical separation catalyst for synthesizing synthesis intermediates in the field of fine chemicals, making it possible to both safely and easily obtain the R form or S form of optically active alcohols with high purity.

EXAMPLE 2 (SOY BEAN PROTEIN)

The first step of extraction of soy bean water-soluble protein and the second step of immobilization were the same as in Example 1. In the third step, after washing soy bean-calcium arginate gel beads with distilled water at a temperature of 35° C., substrate racemic alcohols consisting of -1-(4-bromophenyl)ethanol, 1-(4-methoxyphenyl) ethanol, 1-(4-nitrophenyl)ethanol and 1(2-naphthyl)ethanol were added followed by substrate conversion by respectively setting the conditions of the shake incubator to 55 rpm. After going through the fourth and fifth steps using the same conditions as those used for green pea protein, evaluation of the resulting optically active alcohols was performed in the same manner as during evaluation of green pea protein.

Synthesis of (R)-1-(4-bromophenyl)ethanol

As shown here, the biochemical conversion reaction of immobilized soy bean protein for the substrate (±)-1-(4-bromophenyl)ethanol (200 mg) requires 2 days by going through bioconversion to 4-bromoacetophenone accompanying sterically selective oxidation of (S)-1-(4-bromophenyl)ethanol to obtain 108 mg of (R)-1-(4-bromophenyl)ethanol at a yield of 54%. Optical purity was obtained at 88% e.e. Equipment conditions were the same as for immobilized green pea protein.

Synthesis of (R)-1-(4-chlorophenyl)ethanol

As shown here, the biochemical conversion reaction of immobilized soy bean protein for the substrate (±)-1-(4-chlorophenyl)ethanol (200 mg) requires 3 days by going through bioconversion to 4-chloroacetophenone accompanying sterically selective oxidation of (S)-1-(4-chlorophenyl)ethanol to obtain 102 mg of (R)-1-(4-chlorophenyl)ethanol at a yield of 51%. Optical purity was obtained at 96% e.e.

Synthesis of (R)-1-(4-methoxyphenyl)ethanol

As shown here, the biochemical conversion reaction of immobilized soy bean protein for the substrate (±)-1-(4-methoxyphenyl)ethanol (200 mg) requires 5 days by going through bioconversion to 4-methoxyacetophenone accompanying sterically selective oxidation of (S)-1-(4-methoxyphenyl)ethanol to obtain 96 mg of (R)-1-(4-methoxyphenyl)ethanol at a yield of 48%. Optical purity was obtained at 97% e.e.

Synthesis of (S)-1-(4-nitrophenyl)ethanol

As shown here, the biochemical conversion reaction of immobilized soy bean protein for the substrate (+)-1-(4-nitrophenyl)ethanol (200 mg) requires 4 days by going through bioconversion to 4-nitroacetophenone accompanying sterically selective oxidation of (R)-1-(4-nitrophenyl) ethanol to obtain 90 mg of (S)-1-(4-nitrophenyl)ethanol at a yield of 45%. Optical purity was obtained at 99% e.e.

Next, the results of synthesizing the above-mentioned optically active alcohols using immobilized soy bean protein as optical separation catalyst are shown in the following table.

| | Grain and Bean Protein Soy Beans | Optically Active Alcohol (Chiral Product) | Yield (%) | Optical Purity (% e.e.) |
|---|---|---|---|---|
| 1 | Glycine max. | (R)-1-(4-bromophenyl) ethanol | 54 | 82 |
| 2 | Glycine max. | (R)-1-(4-chlorophenyl) ethanol | 51 | 91 |
| 3 | Glycine max. | (R)-1-(4-methoxyphenyl) ethanol | 48 | 99 |
| 4 | Glycine max. | (S)-1-(4-nitrophenyl) ethanol | 45 | 99 |
| 5 | Glycine max. | (S)-1-(2-naphthyl)ethanol | 49 | 99 |

On the basis of the above, soy bean water-soluble protein was found to be effective as an optical separation catalyst for synthesizing synthesis intermediates in the field of fine chemicals, making it possible to both safely and easily obtain the R form or S form of optically active alcohols with high purity.

EXAMPLE 3 (BUCKWHEAT PROTEIN)

In the extraction of buckwheat water-soluble protein in the first step, after removing food fiber by treating in the same manner as the green pea protein of Example 1, isoelectric precipitation was performed under alkaline conditions (around pH 9.5) to obtain buckwheat water-soluble protein using the same procedure as green pea protein. In the second step, the procedure of Example 1 was performed to obtain buckwheat protein-calcium arginate gel beads. In the third step, after making the temperature of the distilled water 35° C., substrate racemic alcohol was added in the same manner as Example 2 for the substrate racemic alcohol, followed by evaluation of the optically active alcohols obtained by going through the fourth and fifth steps.

Synthesis of (R)-1-(4-bromophenyl)ethanol

As shown here, the biochemical conversion reaction of immobilized buckwheat protein for the substrate (±)-1-(4-bromophenyl)ethanol (200 mg) requires 11 days by going through bioconversion to 4-bromoacetophenone accompanying sterically selective oxidation of (S)-1-(4-bromophenyl)ethanol to obtain 114 mg of (R)-1-(4-bromophenyl)ethanol at a yield of 57%. Optical purity was obtained at 88% e.e.

Synthesis of (R)-1-(4-chlorophenyl)ethanol

As shown here, the biochemical conversion reaction of immobilized buckwheat protein for the substrate (±)-1-(4-chlorophenyl)ethanol (200 mg) requires 13 days by going through bioconversion to 4-chloroacetophenone accompanying sterically selective oxidation of (S)-1-(4-chlorophenyl)ethanol to obtain 116 mg of (R)-1-(4-chlorophenyl)ethanol at a yield of 58%. Optical purity was obtained at 91% e.e.

Synthesis of (R)-1-(4-methoxyphenyl)ethanol

As shown here, the biochemical conversion reaction of immobilized buckwheat protein for the substrate (±)-1-(4-methoxyphenyl)ethanol (200 mg) requires 6 days by going through bioconversion to 4-methoxyacetophenone accompanying sterically selective oxidation of (S)-1-(4-methoxyphenyl)ethanol to obtain 112 mg of (R)-1-(4-methoxyphenyl)ethanol at a yield of 46%. Optical purity was obtained at 99% e.e.

Synthesis of (S)-1-(4-nitrophenyl)ethanol

As shown here, the biochemical conversion reaction of immobilized buckwheat protein for the substrate (±)-1-(4-nitrophenyl)ethanol (200 mg) requires 17 days by going through bioconversion to 4-nitroacetophenone accompanying sterically selective oxidation of (R)-1-(4-nitrophenyl)ethanol to obtain 50 mg of (S)-1-(4-nitrophenyl)ethanol at a yield of 25%. Optical purity was obtained at 99% e.e.

Next, the results of synthesizing the above-mentioned optically active alcohols using immobilized buckwheat protein as optical separation catalyst are shown in the following table.

|   | Grain and Bean Protein Buckwheat | Optically Active Alcohol (Chiral Product) | Yield (%) | Optical Purity (% e.e.) |
|---|---|---|---|---|
| 1 | Fagopyrum esculentum. | (R)-1-(4-bromophenyl)ethanol | 57 | 88 |
| 2 | Fagopyrum esculentum. | (R)-1-(4-chlorophenyl)ethanol | 58 | 96 |
| 3 | Fagopyrum esculentum. | (R)-1-(4-methoxyphenyl)ethanol | 46 | 99 |
| 4 | Fagopyrum esculentum. | (S)-1-(4-nitrophenyl)ethanol | 25 | 99 |
| 5 | Fagopyrum esculentum. | (S)-1-(2-naphthyl)ethanol | 50 | 99 |

On the basis of the above, buckwheat water-soluble protein was found to be effective as an optical separation catalyst for synthesizing synthesis intermediates in the field of fine chemicals, making it possible to both safely and easily obtain the R form or S form of optically active alcohols with high purity.

EXAMPLE 4 (EFFECTIVENESS OF CONTINUOUS RECYCLING OF GREEN PEA, SOY BEAN AND BUCKWHEAT PROTEIN)

With respect to the effectiveness of the first round of the second through fifth steps using green pea, soy bean and buckwheat protein prepared in the first step, as indicated in Examples 1 through 3, the proteins were found to be effective as optical separation catalysts that can be adequately used as synthesis intermediates in the field of fine chemicals, making it possible to both safely and easily obtain the R form or S form of optically active alcohols with high purity. Example 4 describes the results of assessing the effectiveness of repeated recycling of immobilized green pea, soy bean and buckwheat protein.

Figure 2:
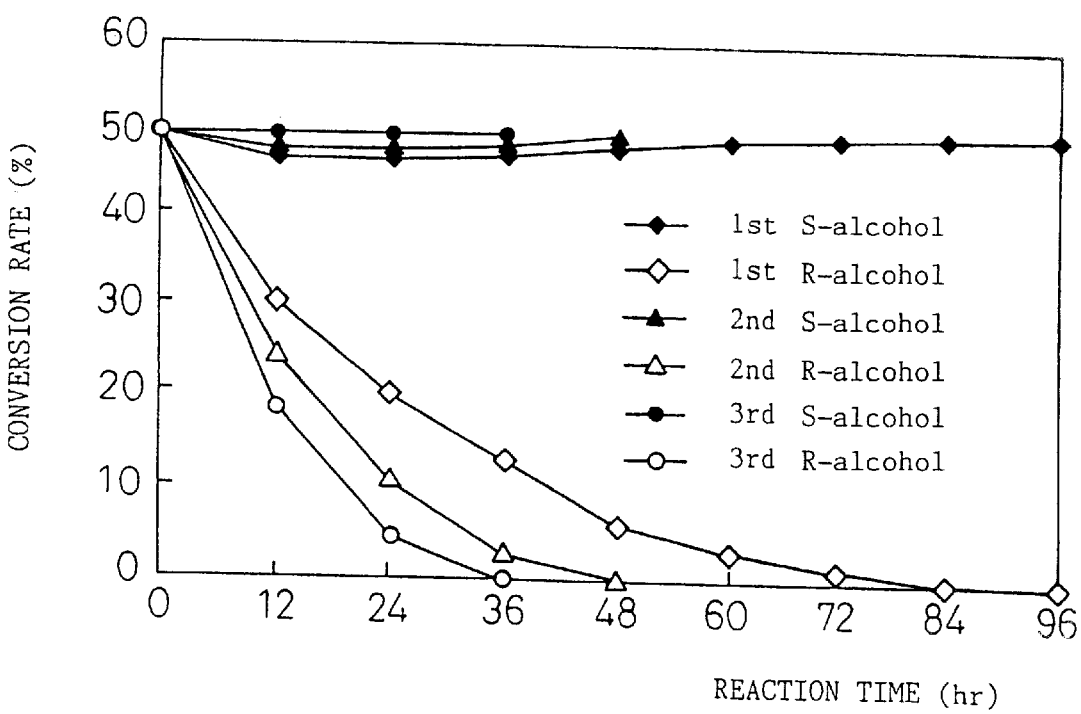
FIG. 2 is a graph indicating the relationship between reaction time and formation conversion rate for each of the 1st to 3rd cycles of the reaction of FIG. 1 by indicating the efficacy of the immobilized water-soluble protein of the present invention when used continuously.

As shown in FIG. 2, according to the results of Example 1, immobilized green pea protein was used in the first round to sterically selectively convert the R form of the racemer 1-(2-naphthyl)ethanol to 2-acetonaphthone and synthesize the remaining S form of 1-(2-naphthyl)ethanol at a high optical purity of 99% e.e or higher. In the fourth step following completion of the reaction, used immobilized green pea protein was continuously recycled and according to the results of attempting a similar reaction starting from the third step, as shown in FIG. 2, (S)-1-(2-naphthyl)ethanol was biosynthesized at a high optical purity of 99% e.e or higher in roughly half the reaction time of the first round. Moreover, as a result of similarly attempting a third round of the reaction, (S)-1-(2-naphthyl)ethanol was biosynthesized at a high optical purity of 99% e.e. or higher in roughly 3/8 the reaction time.

Next, the results of synthesis of the substrate 1-(2-naphthyl)ethanol by continuous recycling of immobilized green pea protein are shown below.

| Continuous Recycling | Reaction Time (hr) | Steric Configuration | Optical Purity | Chemical Yield |
|---|---|---|---|---|
| 1st Round | 96 | S | 99 | 50 |
| 2nd Round | 48 | S | 99 | 50 |
| 3rd Round | 36 | S | 99 | 50 |

On the basis of the above, green pea protein was found to be effective as an optical separation catalyst for synthesizing synthesis intermediates in the field of fine chemicals, enabling large-volume synthesis as a result of being able to be reused, and allowing the R form or S form of optically active alcohols to be obtained both safely and easily with high purity.

Moreover, in Example 2, the biochemical conversion reaction of immobilized soy bean protein for the substrate (±)-1-(4-methoxyphenyl)ethanol (200 mg) required 2 days by going through bioconversion to 4-methoxyacetophenone accompanying sterically selective oxidation of (R)-1-(4-methoxyphenyl)ethanol to obtain 100 mg of (R)-1-(4-methoxyphenyl)ethanol at a yield of 50% and optical purity of 99% e.e. or higher. In Example 4, as a result of studying a similar reaction of immobilized soy bean protein used in the fourth step resuming from the third step using the substrate (±)-1-(4-methoxyphenyl)ethanol, (R)-1-(4-methoxyphenyl)ethanol was biosynthesized at a high optical purity of 99% e.e. or higher in roughly half the reaction time of the first round. Moreover, as a result attempting a third round of the same reaction, (R)-1-(4-methoxyphenyl)ethanol was biosynthesized at a high optical purity of 99% e.e. or higher in half the reaction time of the first round.

Next, the results of synthesis of the substrate 1-(4-methoxyphenyl)ethanol by continuous recycling of immobilized soy bean protein are shown below.

| Continuous Recycling | Reaction Time (hr) | Steric Configuration | Optical Purity | Chemical Yield |
|---|---|---|---|---|
| 1st Round | 48 | R | 99 | 50 |
| 2nd Round | 24 | R | 99 | 50 |
| 3rd Round | 24 | R | 99 | 49 |

On the basis of the above, soy bean protein was found to be effective as an optical separation catalyst for synthesizing synthesis intermediates in the field of fine chemicals, enabling large-volume synthesis as a result of being able to be reused, and allowing the R form or S form of optically active alcohols to be obtained both safely and easily with high purity.

In Example 3, the biochemical conversion reaction of immobilized buckwheat protein for the substrate (±)-1-(2-naphthyl)ethanol (200 mg) required 4 days by going through bioconversion to 2-acetonaphthone accompanying sterically selective oxidation of (R)-1-(2-naphthyl)ethanol to obtain 100 mg of (S)-1-(2-naphthyl)ethanol at a yield of 50% and optical purity of 99% e.e. or higher. In Example 4, as a result of reacting with the substrate (±)-1-(2-naphthyl)ethanol by continuously recycling immobilized buckwheat protein used in this fourth step from the third step, optically active (S)-1-(2-naphthyl)ethanol was obtained at an optical purity of 99% e.e. or higher by going through a conversion mechanism which sterically selectively converts (R)-1-(2-naphthyl)ethanol to 2-acetonaphthone in the same manner as the first round. Continuous recycling of immobilized buckwheat protein maintained effectiveness for at least three rounds, and there were no changes observed in reaction time, chemical yield or optical purity.

Next, the results of synthesis of the substrate 1-(2-naphthyl)ethanol by continuous recycling of immobilized buckwheat protein are shown below. On the basis of the above, buckwheat protein was found to be effective as an optical separation catalyst for synthesizing synthesis intermediates in the field of fine chemicals, enabling large-volume synthesis as a result of being able to be reused, and allowing the R form or S form of optically active alcohols to be obtained both safely and easily with high purity.

| Continuous Recycling | Reaction Time (hr) | Steric Configuration | Optical Purity | Chemical Yield |
|---|---|---|---|---|
| 1st Round | 96 | S | 99 | 50 |
| 2nd Round | 96 | S | 99 | 50 |
| 3rd Round | 96 | S | 99 | 50 |

EXAMPLE 5 (TARTARY BUCKWHEAT PROTEIN)

A ground powder of tartary buckwheat was passed through a 12 mesh sieve to remove large particles and husks. The water-soluble protein of ground powder obtained in this manner was then extracted for 45 minutes using an amount of distilled water equal to approximately 9 times the weight of the powder at about 40° C. and pH 7.0. Food fibers were separated from this extract using a decanter to obtain protein curd. 20 g of this protein curd were measured out followed by breaking up in a mixer in 200 ml of distilled water equal to 10 times the weight of the protein curd to prepare a protein slurry.

Immobilized beads were obtained using this slurry in the same manner as the second step of Example 1.
Synthesis of (S)-1-phenylethanol from ±-1-phenylethanol Continuing, using these immobilized beads as catalyst, 400 ml of distilled water equal to 20 times the weight of tartary buckwheat curd were added as reaction solvent. After making the temperature of the distilled water 35° C. using a constant-temperature shaking culturing vessel, 201 mg of ±-1-phenylethanol were added as substrate after which the conditions of the culturing vessel were set to 55 rpm and substrate conversion was performed for 8 days. (S)-1-phenylethanol was obtained at a conversion rate of 50%, optical purity of 95% e.e. and yield of 42% by going through the fourth and fifth steps under similar conditions as used with green pea protein. The yield of the formed acetophenone was 51% (102 mg).

Process for Producing Optically Active Alcohols by Asymmetric Reduction Using the Ketone Molecule of (2) as Substrate

EXAMPLE 6 (BUCKWHEAT PROTEIN)

Immobilized beads were obtained from ground buckwheat powder in the same manner as Example 5.
Synthesis of (S)-1-phenylethanol from Acetophenone Continuing, using these immobilized beads as catalyst, 400 ml of distilled water equal to 20 times the weight of buckwheat curd were added as reaction solvent. After making the temperature of the distilled water 35° C. using a constant-temperature shake culturing vessel, 202 mg of acetophenone were added as substrate after which the conditions of the culturing vessel were set to 55 rpm and substrate conversion was performed. For the fourth step, the conversion product was extracted with diethyl ether, and for the fifth step, isolation and purification were performed using a silica gel chromatograph (70–230 mesh) and hexane:ethyl acetate=9:1 for the developing solvent. The residual acetophenone was 50%. The reaction conditions, conversion rate, optical purity, yield and steric configuration of the resulting phenylethanol are shown in the following table.

EXAMPLES 7–12
Synthesis of (S)-1-phenylethanol from Acetophenone

Substrate conversion of acetophenone was performed in the same manner as Example 6 using amaranth powder, kidney bean powder, barnyard millet powder, foxtail millet powder and tartary buckwheat powder. The residual acetophenone was 55%, 51%, 45%, 11% and 51%, respectively. The reaction time, conversion rates, optical purities, yields and steric configurations of the resulting phenylethanol are shown in the following table.

| Grain | Reaction Time (days) | Conversion Rate (%) | Yield (%) | Optical Purity (% e.e.) | Steric Configuration |
|---|---|---|---|---|---|
| Ordinary buckwheat powder | 6 | 34 | 30 | 66 | S |
| Amaranth powder | 7 | 21 | 20 | 97 | S |
| Kidney bean powder | 7 | 30 | 25 | 15 | S |
| Barnyard millet powder | 4 | 50 | 33 | 96 | S |
| Foxtail millet powder | 4 | 85 | 60 | 62 | S |
| Tartary buckwheat powder | 7 | 40 | 22 | 97 | S |

Synthesis of (S)-1-(2-naphthyl)ethanol from 2-acetonaphthone

EXAMPLE 13 (TARTARY BUCKWHEAT POWDER PROTEIN)

300 g of tartary buckwheat powder were extracted in 2000 ml of water for 45 minutes at about 40° C. followed by centrifugal separation of the water-soluble component at 7000 rpm/min for 20 minutes. Immobilized beads were then prepared from the resulting precipitate (solid) in the same manner as Example 1. When reacted for 4 days in the same manner as Example 5 using 203 mg of 2-acetylnaphthone as substrate, (S)-1-(2-naphthyl)ethanol was biosynthesized at a yield of 11% (105 mg). As a result of performing HPLC analysis of (S)-1-(2-naphthyl)ethanol using a chiral cell OB (Daicel Chemical Industries) in a developing solvent of hexane:2-propanol=9:1 after setting the flow rate to 0.5 cm$^3$/min and optical absorbance to 254 nm, absorption of 99.9% of the S alcohol was able to be confirmed at a retention time of 20.8 minutes, while absorption of 0.1% of the R alcohol was confirmed at a retention time of 23.8 minutes.

INDUSTRIAL APPLICABILITY

High-purity R or S forms of optically active alcohols that can be sufficiently used as catalysts for synthesizing synthesis intermediates in the field of fine chemicals can be obtained both safely and easily by combining a first step comprising extracting water-soluble protein from grains or beans, a second step comprising immobilization of the above-mentioned protein, a third step comprising performing an enzyme conversion reaction on a substrate serving as the raw material using the above-mentioned immobilized protein as catalyst, a fourth step comprising extracting the above-mentioned reaction substrate converted by said third step and the reaction product with organic solvent, and a fifth step comprising isolating and purifying optically active alcohol or the acylated form of optically active alcohol from the reaction substrate and reaction product extracted in said fourth step, followed additionally by hydrolysis as necessary.

What is claimed is:

1. A process of producing optically active alcohol comprising a first step comprising extracting water-soluble protein from grains or beans, a second step comprising immobilization of the above-mentioned protein, a third step comprising enzyme conversion reaction of a substrate serving as raw material using said protein as catalyst with a non-polar or polar solvent, a fourth step comprising extracting the reaction mixture converted by said third step using organic solvent, and a fifth step comprising isolating and purifying optically active alcohol or the acylated form of optically active alcohol from the extract of said fourth step, followed additionally by a hydrolysis step as necessary.

2. A process of producing optically active alcohol as set forth in claim 1 wherein said catalyst is a water-soluble protein extracted from grains such as buckwheat, amaranth, rice, wheat, barley, corn, oats, rye, foxtail millet, barnyard millet, millet, adlay and sorghum, or beans such as adsuki beans, kidney beans, green peas, green beans and soy beans.

3. A process of producing optically active alcohol as set forth in claim 1 wherein the substrate of enzyme conversion in said third step is a racemic alcohol and one of its enantiomers is selectively oxidized.

4. A process of producing optically active alcohol as set forth in claim 1 wherein the substrate of enzyme conversion in said third step is a ketone and production is carried out by asymmetric reduction.

5. A process of producing optically active alcohol as set forth in claim 1 wherein the substrate of enzyme conversion in said third step is an acylated form of a racemic alcohol and production is carried out by asymmetric hydrolysis.

6. A process of producing optically active alcohol as set forth in claim 1 wherein the enzyme conversion of said third step is carried out by asymmetric acylation of substrate racemic alcohol using acyl halide or vinyl acetate, the extract in said fourth step is the acylated form of optically active alcohol, and a hydrolysis step is included after said fifth step.

* * * * *